United States Patent
Bove et al.

(10) Patent No.: US 6,322,491 B1
(45) Date of Patent: Nov. 27, 2001

(54) FLEXIBLE MAGNETIC INSOLE

(75) Inventors: Anthony Bove, Port Jefferson; Vincent Ardizzone, Bay Shore, both of NY (US)

(73) Assignee: Nu-Magnetics, Inc., Port Jefferson, NY (US)

(*) Notice: Subject to any disclaimer, the term of this patent is extended or adjusted under 35 U.S.C. 154(b) by 0 days.

(21) Appl. No.: 09/379,826

(22) Filed: Aug. 23, 1999

Related U.S. Application Data (63) Continuation-in-part of application No. 09/038,508, filed on Mar. 10, 1998, which is a continuation-in-part of application No. 08/911,950, filed on Aug. 15, 1997, which is a continuation-in-part of application No. 08/678,348, filed on Jul. 11, 1996, now Pat. No. 5,714,704, and a continuation-in-part of application No. 08/565,826, filed on Dec. 1, 1995, now abandoned, which is a continuation of application No. 08/573,390, filed on Dec. 15, 1995, now Pat. No. 5,538,495, which is a continuation of application No. 08/427,733, filed on Apr. 24, 1995, now Pat. No. 5,514,072, which is a continuation of application No. 08/276,876, filed on Jul. 18, 1994, now abandoned, which is a continuation of application No. 08/158,607, filed on Nov. 29, 1993, now abandoned, which is a continuation of application No. 07/990,927, filed on Dec. 14, 1992, now Pat. No. 5,277,692, which is a continuation of application No. 07/823,149, filed on Jan. 21, 1992, now abandoned (60) Provisional application No. 60/118,832, filed on Feb. 5, 1999.

(51) Int. Cl.[7] ........................................ A61N 1/00
(52) U.S. Cl. ................................................ 600/15
(58) Field of Search ............................ 600/9–15

(56) References Cited

U.S. PATENT DOCUMENTS

| | | | |
|---|---|---|---|
| 4,240,437 | 12/1980 | Church | 128/420 R |
| 4,401,961 | 8/1983 | Baermann et al. | 335/285 |
| 4,489,711 | 12/1984 | Latzke | 128/1.3 |
| 4,549,532 | * 10/1985 | Baermann | 600/15 |
| 4,550,714 | 11/1985 | Talish et al. | 128/1.5 |
| 4,587,956 | 5/1986 | Griffin et al. | 128/1.3 |
| 4,731,297 | 3/1988 | Takaya | 428/553 |
| 4,798,194 | 1/1989 | Amishima | 128/9 |
| 5,017,185 | 5/1991 | Baermann | 600/15 |
| 5,045,050 | 9/1991 | Liboff et al. | 600/9 |
| 5,067,940 | 11/1991 | Liboff et al. | 600/13 |
| 5,084,003 | 1/1992 | Susic | 600/13 |

(List continued on next page.)

FOREIGN PATENT DOCUMENTS

| | | | |
|---|---|---|---|
| 8301728 | * 12/1984 | (NL) | 600/15 |
| 94/13357 | 6/1994 | (WO) | A61N/1/00 |
| 84/00305 | 2/1984 | (WO) | A61N/1/42 |

*Primary Examiner*—John P. Lacyk

(57) ABSTRACT

A magnetic insole provides magnetotherapy for the soles of a wearer's feet. A laminated insole in the general shape of a foot is inserted into a shoe to provide magnetotherapy to the wearer's foot adjacent the sole. Collateral therapeutic effects may be effected as such magnetotherapy may affect the nerve endings in the foot and collateral, corresponding, or related tissue structures in the body. A leather upper is used to bear the abrasion between the foot and the magnetic insole. A flexible magnetic core provides alternating magnetic fields in a regular pattern thereby to provide magnetotherapy to the foot. A cushioning base acts as an underpad for the magnetic insole in order to provide greater comfort and cushioning for the user's foot. The flexible magnetic core is constructed by mixing strontium ferrite, barium ferrite, or other strongly ferromagnetic material and with an elastic binder such as neoprene. Additional minor constituents are also added to aid processing. The ferromagnetic material-elastic mixture is mixed together on a two (2) roll rubber mill as is known in the art, pigged, calendared, magnetized, and cut to size. The resulting sheet may then be laminated on its top side by leather upper material and on the bottom side by cushioning material so as to provide a three (3) layer laminated sheet from which magnetic insoles of the present invention may be cut and perforated.

11 Claims, 8 Drawing Sheets

U.S. PATENT DOCUMENTS

| | | | |
|---|---|---|---|
| 5,085,626 | 2/1992 | Frey | 600/13 |
| 5,092,835 | 3/1992 | Schurig et al. | 600/9 |
| 5,195,941 | 3/1993 | Erickson et al. | 600/14 |
| 5,226,020 | 7/1993 | Li et al. | 368/10 |
| 5,226,185 | 7/1993 | Guay et al. | 5/448 |
| 5,233,768 * | 8/1993 | Humphreys | 600/15 |
| 5,266,914 | 11/1993 | Dickson et al. | 335/288 |
| 5,267,939 | 12/1993 | Liboff et al. | 600/13 |
| 5,277,692 | 1/1994 | Ardizzone | 600/9 |
| 5,295,494 | 3/1994 | Rodriguez | 128/845 |
| 5,304,111 | 4/1994 | Mitsuno et al. | 600/9 |
| 5,312,321 | 5/1994 | Holcomb | 600/9 |
| 5,314,401 | 5/1994 | Tepper | 600/14 |
| 5,389,061 | 2/1995 | Nor | 600/15 |
| 5,426,925 | 6/1995 | Smargiassi | 54/79.1 |
| 5,450,858 | 9/1995 | Zablotsky et al. | 128/876 |
| 5,453,073 | 9/1995 | Markoll | 600/14 |
| 5,459,445 | 10/1995 | Je | 335/214 |
| 5,478,303 | 12/1995 | Foley-Nolan et al. | 600/15 |
| 5,514,072 | 5/1996 | Ardizzone | 600/9 |
| 5,538,495 | 7/1996 | Ardizzone | 600/9 |
| 5,626,099 | 5/1997 | Staller et al. | 119/625 |
| 5,632,720 | 5/1997 | Kleitz | 601/15 |
| 5,642,739 | 7/1997 | Fareed | 128/881 |
| 5,665,049 | 9/1997 | Markoll | 600/14 |
| 5,700,234 | 12/1997 | Masuda | 600/15 |
| 5,707,333 | 1/1998 | Bakst | 600/9 |
| 5,709,223 | 1/1998 | Rawls, Jr. et al. | 128/898 |
| 5,714,927 | 2/1998 | Henderson et al. | 340/435 |
| 5,728,058 | 3/1998 | Ouellette et al. | 602/62 |
| 5,738,624 | 4/1998 | Zablotsky et al. | 600/9 |
| 5,766,236 | 6/1998 | Detty et al. | 607/149 |
| 5,782,743 | 7/1998 | Russell | 600/9 |

* cited by examiner

```
CREATE AND PREPARE LAMINATED
SHEET OF LEATHER UPPER, FLEXIBLE
MAGNETIC CORE, AND CUSHIONING
BASE
                                    70
```

```
CUT INSOLE SECTION PAIRS FROM
        LAMINATE SHEET
                                    72
```

```
    PERFORATE INSOLE SECTIONS
                                    74
```

FIG. 3

| PREPARE MIXTURE BY MIXING ON TWO-ROLL MILL | 80 |

| PREPARE PIGS FROM ROLLED MATERIAL | 82 |

| CALENDAR PIGS TO CREATE SHEET | 84 |

| APPLY NYLON MESH | 86 |

| MAGNETIZE | 88 |

| FORM INTO LAMINATE WITH UPPER AND BASE | 90 |

FIG. 4

| N | S | N | S | N |
|---|---|---|---|---|
| S | N | S | N | S |
| N | S | N | S | N |
| S | N | S | N | S |
| N | S | N | S | N |

FLEXIBLE MAGNETIC INSOLE

CROSS-REFERENCES TO RELATED APPLICATIONS

This application is related to U.S. provisional patent application Ser. No. 60/118,832 filed Feb. 5, 1999 for a Magnetic Insole and Method of Manufacture. This application is a continuation-in-part application of U.S. patent application Ser. No. 09/038,508 filed Mar. 10, 1998 pending, which is a continuation-in-part of U. S. patent application Ser. No. 08/911,950 filed Aug. 15, 1997 pending, which is a continuation-in-part application of U.S. patent application Ser. No. 08/678,348 filed Jul. 11, 1996 now U.S. Pat. No. 5,714,704, which is a continuation of application Ser. No. 08/573,390, filed Dec. 15, 1995, now U.S. Pat. No. 5,538, 495 which is a continuation of application Ser. No. 08/427, 733, filed Apr. 24, 1995, now U.S. Pat. No. 5,514,072, which is a continuation of application Ser. No. 08/276,876, filed Jul. 18, 1994, now abandoned, which is a continuation of application Ser. No. 08/158,607, filed Nov. 29, 1993, now abandoned, which is a continuation of application Ser. No. 07/990,927, filed Dec. 14, 1992, now U.S. Pat. No. 5,277, 692, which is a continuation of application Ser. No. 07/823, 149, filed Jan. 21, 1992, now abandoned. This application is also a continuation-in-part of U.S. patent application Ser. No. 08/565,826 filed Dec. 1, 1995. The contents of all applications of which the present application is a divisional, continuation, continuation-in-part, or otherwise from which this application is related are incorporated herein by this reference thereto.

BACKGROUND OF THE INVENTION

Field of the Invention

This invention relates to magnetotherapeutic devices, and more particularly to a magnetotherapeutic insole for a shoe or the like and a method for manufacturing a flexible magnetic core for the same.

Description of the Related Art

Magnetotherapy uses magnetic fields to provide therapeutic and restorative treatment to limbs, organs, and other parts of the body. Generally, one means by which magnetotherapy may be achieved is by bringing a magnet or a series of magnets into close proximity to the affected body part or organ of interest. As is known according to Faraday's Law of Magnetic Induction, as well as the Hall Effect, charged particles experience a force acting on them when they move through a magnetic field in a perpendicular direction. Since human blood is replete with ions and electrolytes, it has many charged molecules, particles, and the like which experience a force, including an aligning force, when moving through a magnetic field. When exposed and caused to so travel through a magnetic field, such ions and electrolytes may generate heat, causing the associated blood vessel to widen. The widening of the blood vessel would then allow increased volumes of blood to flow through the blood vessel.

Polar molecules (such as water) also respond to magnetic fields in a manner similar to that for charged molecules. Additional therapeutic or restorative effects might arise through the alignment of polar molecules as they pass through the magnetic field. When subject to a magnetic field, polar molecules rotate to align themselves with the field. Such alignment would alternate with the magnetic polarity as the polar molecules traveled through different regions of such magnetic polarity. The mechanical motion of the rotation of such polar molecules might also cause heating and the like and would also stimulate, mix, or agitate the blood in a gentle manner, causing it to gently churn. Such mixing of the blood at the molecular level may cause it to more easily recognize foreign matter. By recognizing foreign matter, the blood and/or immune system may be able to more readily address such foreign matter.

Several patents are known having various designs for the alternation of magnets of different polarity to provide spatially diverse magnetic fields. The patent to Latzke (U.S. Pat. No. 4,489,711 issued Dec. 25, 1984) and the patents to Ardizzone (U.S. Pat. No. 5,277,692 issued Jan. 11, 1994; U.S. Pat. No. 5,514,072 issued May 7, 1996; and U.S. Pat. No. 5,538,495 issued Jul. 23, 1996) all disclose a variety of magnetic plaster and magnetic pads having certain magnetic geometries in order to achieve spatially varying magnetic fields through the use of magnets.

In the past, the only way to offer or provide both mechanical support and magnetic therapy was to insert magnets between a brace and the associated body joint. Recently, stronger static magnetic materials have become more readily available in the commercial market. Particularly, permanent magnets incorporating the element neodymium (atomic number 60) provide strong magnetic fields at common temperatures (below 120° F./50° C.). Strontium ferrite also provides a useful magnetic substrate. Barium ferrite also exhibits characteristics useful for a magnetic substrate. Such magnets can be incorporated into flexible fabrics or the like to provide a flexible material suitable for wrapping around joints.

By using flexible and/or elastic materials such as neoprene, nitrile, or SBR, a magnetotherapeutic foot insole previously unseen in the art could be realized. While certain portions of the human body have been emphasized as being subject to the use of magnetotherapeutic devices, it remains to be seen in the art to provide such magnetotherapy in the form of an insole to be worn within shoes or other footwear.

The sole of the foot is known for its sensitivity and for the fact that several nerve endings terminate in the sole of the foot. In some schools of medicinal thought, the sole of the foot provides therapeutic access to other parts of the body due to the connection of the nerves in the foot with such other areas. For example, in Chinese and other Oriental forms of medicine, different areas of the foot may correspond to different areas of the body. Affecting one part of the sole of a person's foot thereby may influence the biological or biochemical activities in other areas of the body. As is known with acupuncture, the stimulation or engagement of nerves, plexus, or the like by long, thin needles may serve to affect other areas of the body. The same may be similarly true with magnetotherapeutic devices when applied to various areas.

Consequently, the art has yet to address ongoing magnetotherapy for the foot, particularly the sole of the foot, which may provide therapeutically advantageous effects not only to the foot area itself, but to the corresponding or collateral areas affected by the nerves or other tissues associated with the sole of the foot.

SUMMARY OF THE INVENTION

A magnetic insole is provided that corresponds to the inside of the shoe or other footwear. The magnetic insole is perforated to allow ventilation and airflow through the magnetic insole. The insole is generally comfortable, providing cushioning and durability, as well as providing magnetotherapy to the underside, or sole, of the person's foot.

The magnetic insole of the present invention is provided by a flexible and highly magnetic core that is sandwiched between a cushioning bottom or base layer and a leather upper. The flexible magnetic core uses strongly magnetic material, such as strontium or barium ferrite, to provide a substrate for the permanent installation of a strong magnetic field.

Proprietary magnetic field arrangements may be invested in the magnetic core portion of the magnetic insole.

Upon fabrication of the magnetic insole of the present invention, the insole is inserted into the shoe or other footwear so that it lies flat upon the last of the shoe. The user's foot then is inserted into the shoe atop the magnetic insole which applies magnetotherapy to the user's foot so long as the user wears the shoe with the magnetic insole.

OBJECTS OF THE INVENTION

It is an object of the present invention to provide a magnetic insole.

It is yet another object of the present invention to provide a magnetic core for a magnetic insole.

It is another object of the present invention to provide a flexible magnetic core for a magnetic insole.

It is another object of the present invention to provide a method by which a flexible magnetic core can be fabricated for a magnetic insole.

It is yet another object of the present invention to provide a cushioned, flexible, and comfortable magnetic insole that allows ventilating airflow through itself.

These and other objects and advantages of the present invention will be apparent from a review of the following specification and accompanying drawings.

DESCRIPTION OF THE PREFERRED EMBODIMENT(S)

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequence may be accomplished by different embodiments that are also intended to be encompassed within the spirit and scope of the invention.

Figure 1:
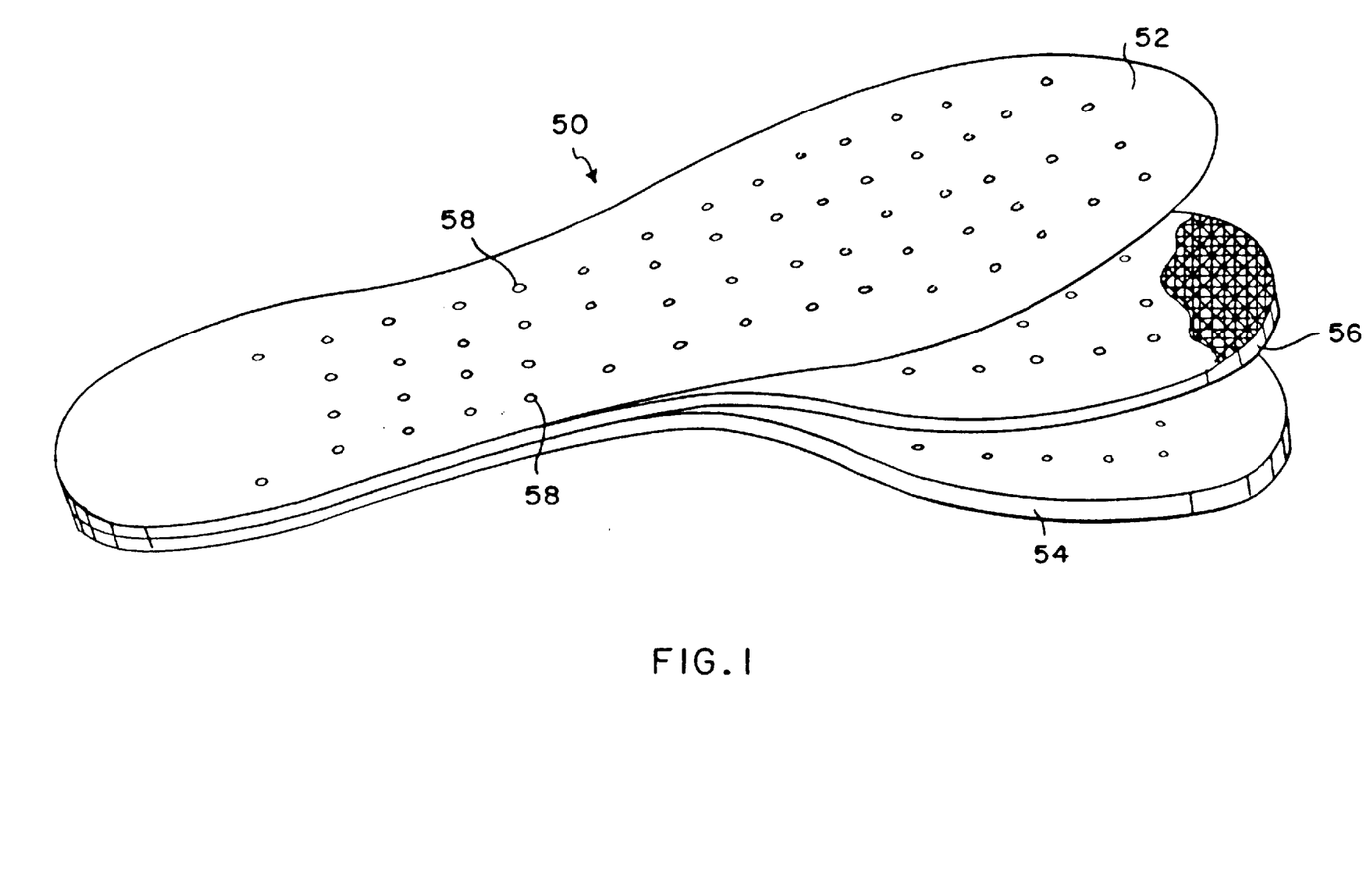
FIG. 1 shows a right perspective view of a right magnetic insole of the present invention. The front end of the magnetic insole is partially delaminated to show the layers. A partial cutaway view of the middle magnetic layer shows alternating magnetic polarity.

As shown in FIG. 1, the flexible magnetic insole 50 of the present invention has a leather upper 52 and a cushioning base 54. A flexible magnetic core 56 is sandwiched between the leather upper 52 and the cushioning base 54.

The leather upper 52 is meant to provide a comfortable and resilient contact surface between the magnetic insole 50 of the present invention and the wearer's foot. Leather is seen as being a most advantageous material to use as it is durable, comfortable, and malleable in order to conform to the specific geometries of the wearer's foot. Other materials having these qualities may also be put to good use, including synthetic materials resembling and wearing like leather. As used herein, the term "leather" indicates all such material usable as leather for the leather upper 52.

The cushioning base 54 may be made of Sorbothane® padding or other similar padding as is available in the art. A durable substance capable of withstanding the inshoe environment is preferable so as to provide good use and wear to the wearer.

As can be seen from FIG. 1, the magnetic insole 50 of the present invention may be approximately one to two-tenths inch ($1/10"-2/10"$) high and shaped to conform to the inside of a shoe. The magnetic insole 50 of the present invention is intended to fit inside the shoe just above the sock liner or other material that would otherwise form the layer of the shoe immediately beneath the sock or foot of the wearer.

As can be seen in FIG. 1, the magnetic insole 50 has a series of perforations 58 that pass through the magnetic insole 50. These perforations 58 serve to allow air to pass through the magnetic insole 50 so that it may ventilate both itself and the underlying portions of the shoe.

Figure 2:
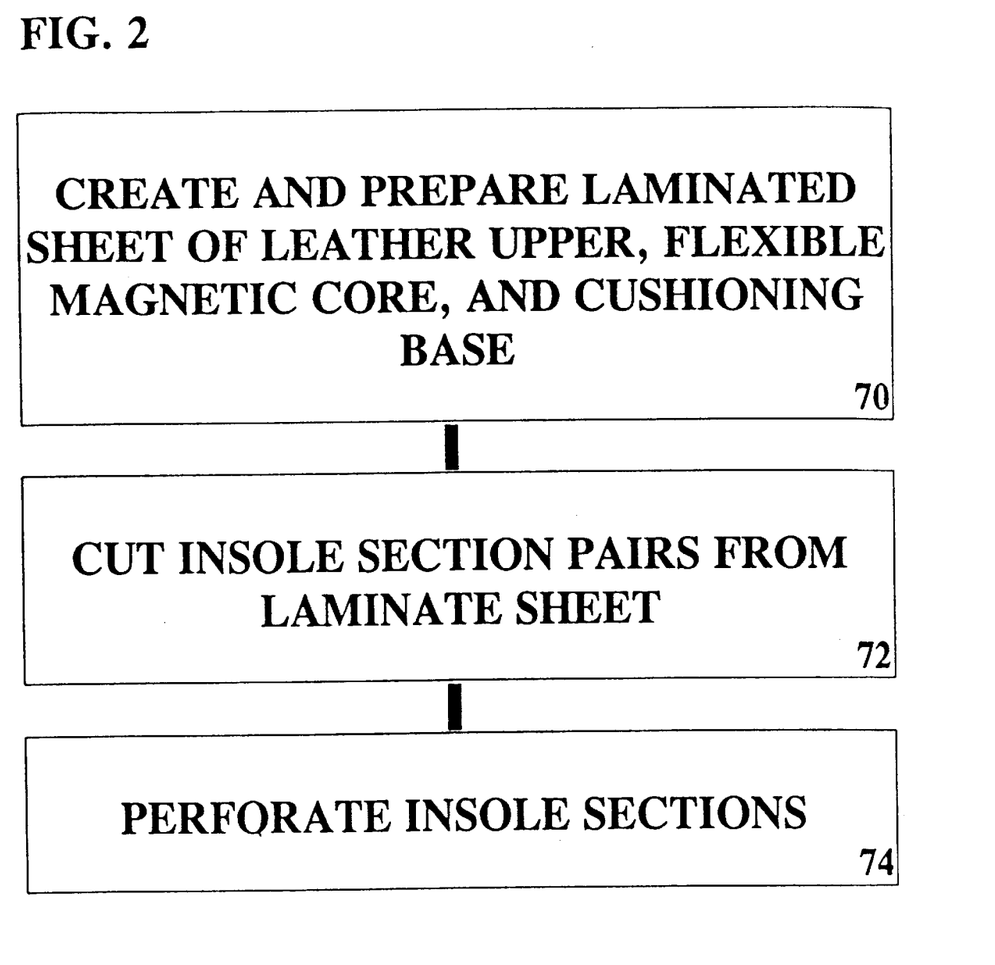
FIG. 2 is a step diagram of the overall method used to create the flexible magnetic insole shown in FIG. 1.

To construct the magnetic insole 50 of the present invention, FIG. 2 shows the basic steps by which the magnetic insole 50 is prepared. In FIG. 2, an initial creation and preparation step 70 is present whereby the individual laminate layers are prepared. A sheet of leather forming the leather upper 52 is provided or selected as is a sheet of flexible magnetic core material and cushioning base material. The sheets are laminated together 70 in order to provide an integrated laminated sheet with the three (3) magnetic insole layers.

Insole sections are then cut 72 from the laminate sheet in order to provide the initial blanks from which the ultimate magnetic insoles 50 will be prepared. As might be assumed, generally the insole sections are cut in pairs for left and right feet, although individual ones of the magnetic insoles for either the left or right foot may be cut separately.

Once an insole pair or single has been made, it is perforated 74 in order to provide the finished product.

In order to provide the flexible magnetic core 56, a very strongly magnetizable material is used in conjunction with a rubber or elastic binder, such as neoprene, nitrile, or SBR. Experience in the craft has developed, indicating that barium or strontium ferrite is one ferromagnetic material that may advantageously be used in the magnetic insole 50 of the present invention.

Approximately eighty-six percent (86%) magnetic ferrite is combined with thirteen percent (13%) elastic binder. The elastic binder serves to make flexible the resulting sheet of magnetic ferrite. Additional ingredients include stearic acid and a mold-release agent such as MoldWiz®. (MoldWiz® is known in the art as manufactured by Axel Plastics Research Laboratories, Inc. Of particular use is that mixture of Mold-Wiz® known in the trade as INT-21G. These additional ingredients provide lubricant for the individual molecular chains). Zinc oxide may be added to provide cross-linking so as to better hold together the magnetic ferrite elastomer mixture, which then sets due to cross-binding and curing.

Figure 3:
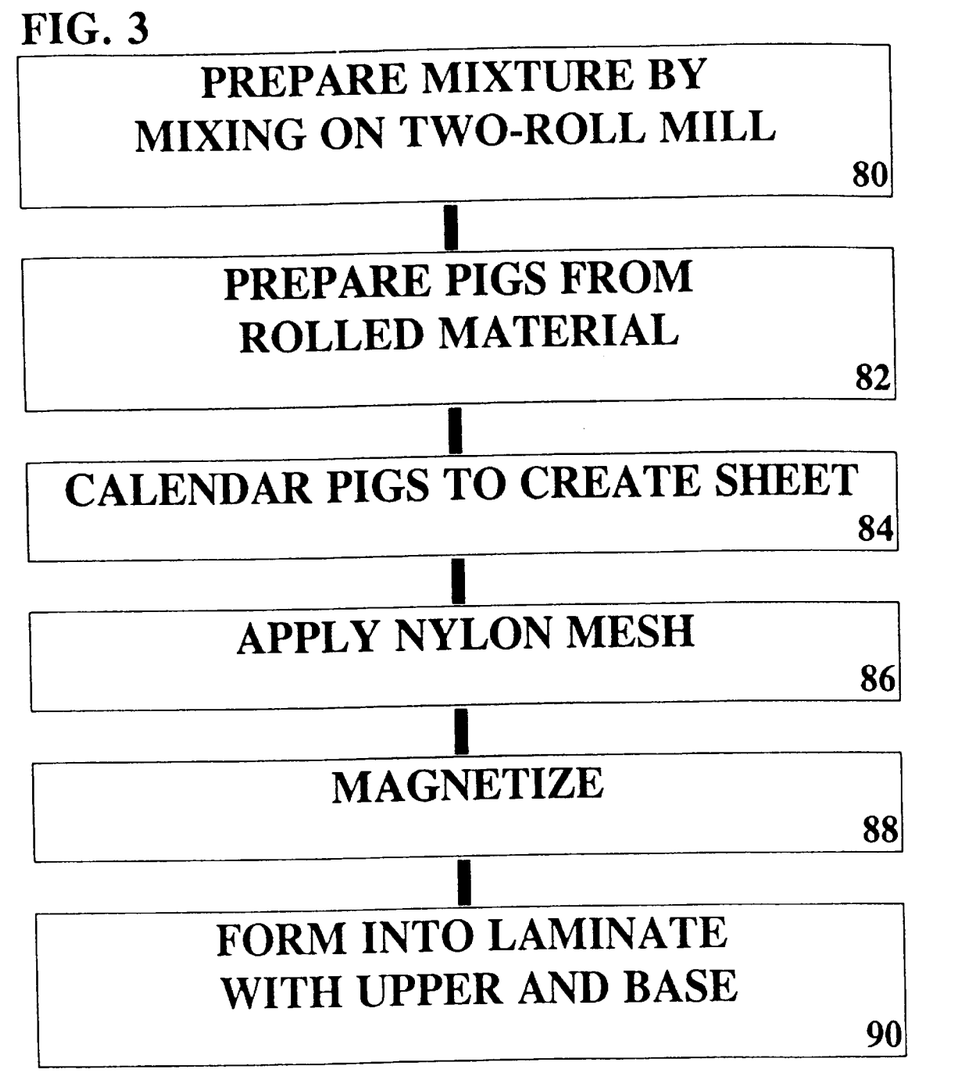
FIG. 3 is a stepwise diagram showing the steps used to create the flexible magnetic core leading up to the flexible magnetic insole of FIG. 1.
Figure 4:
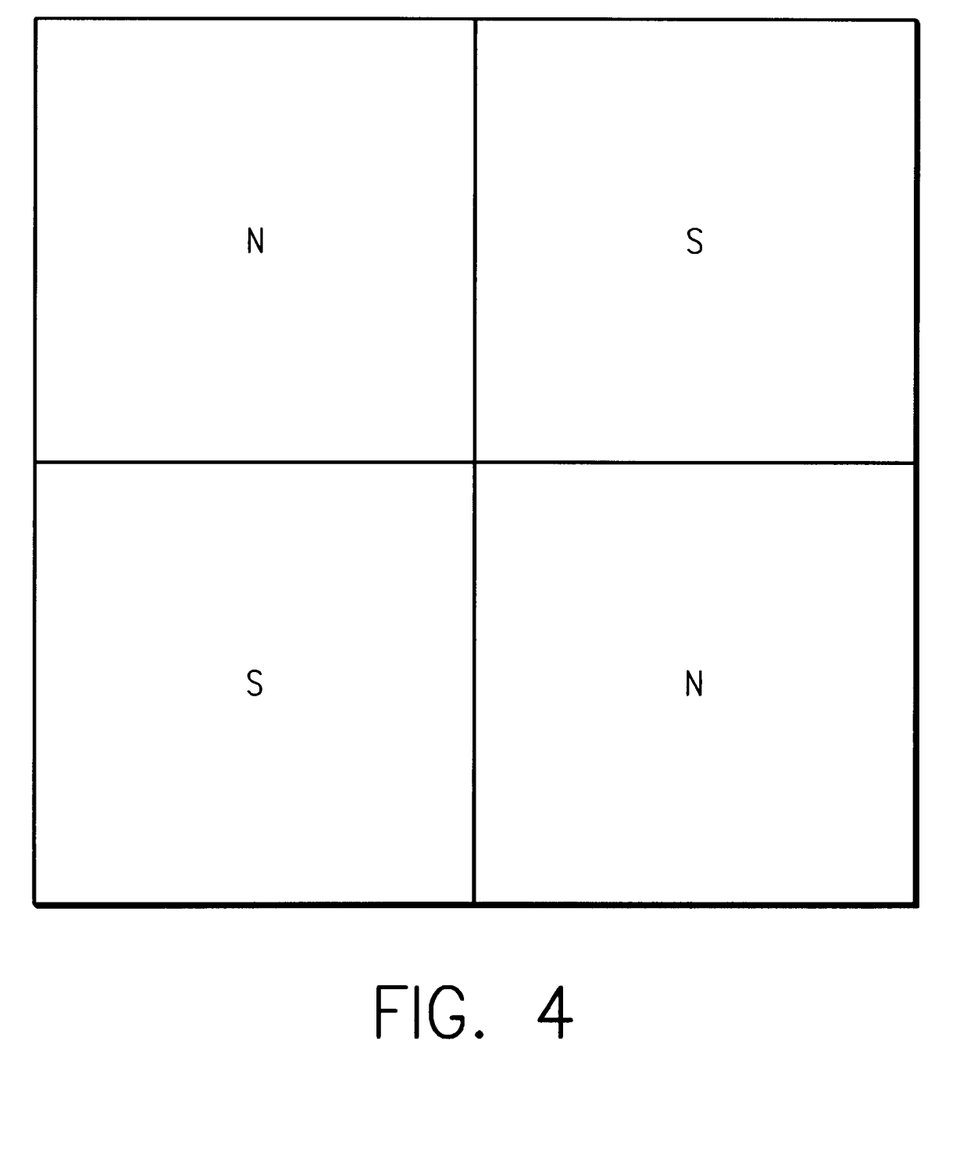
FIG. 4 shows a basic checkerboard configuration of alternating magnetic regions as used in the magnetic insole shown in FIG. 1.
Figure 5:
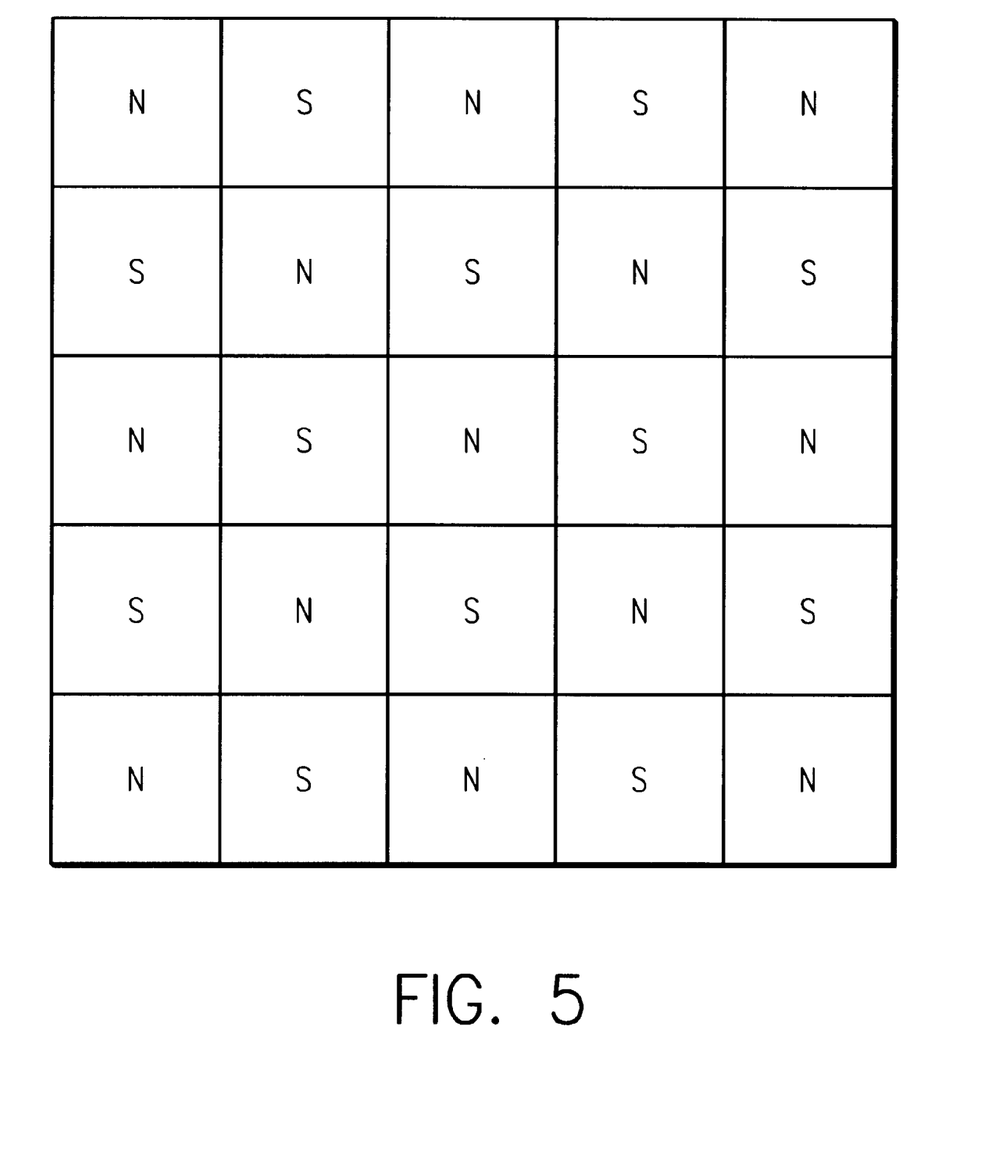
FIG. 5 is an alternating magnetic checkerboard pattern similar to that shown in FIG. 4 that may be used in the flexible magnetic insole of FIG. 1.
Figure 6:
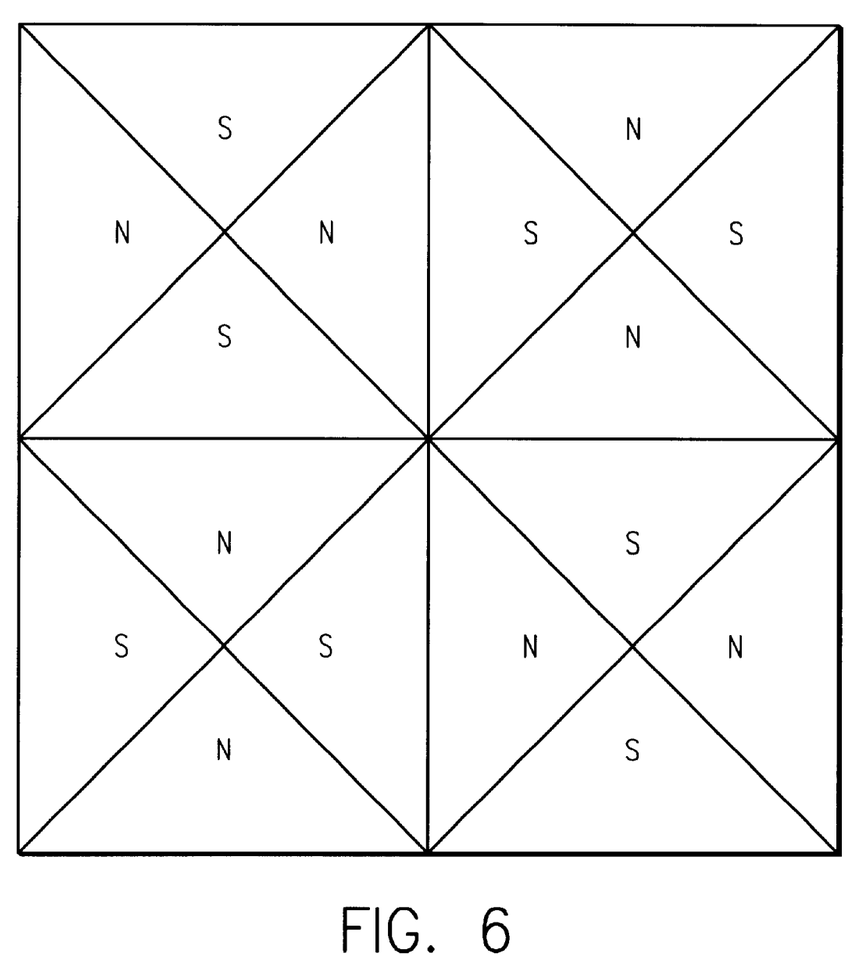
FIGS. 6 and 7 show alternating triangular checkerboard patterns that may be used in the flexible magnetic insole of FIG. 1.
Figure 7:
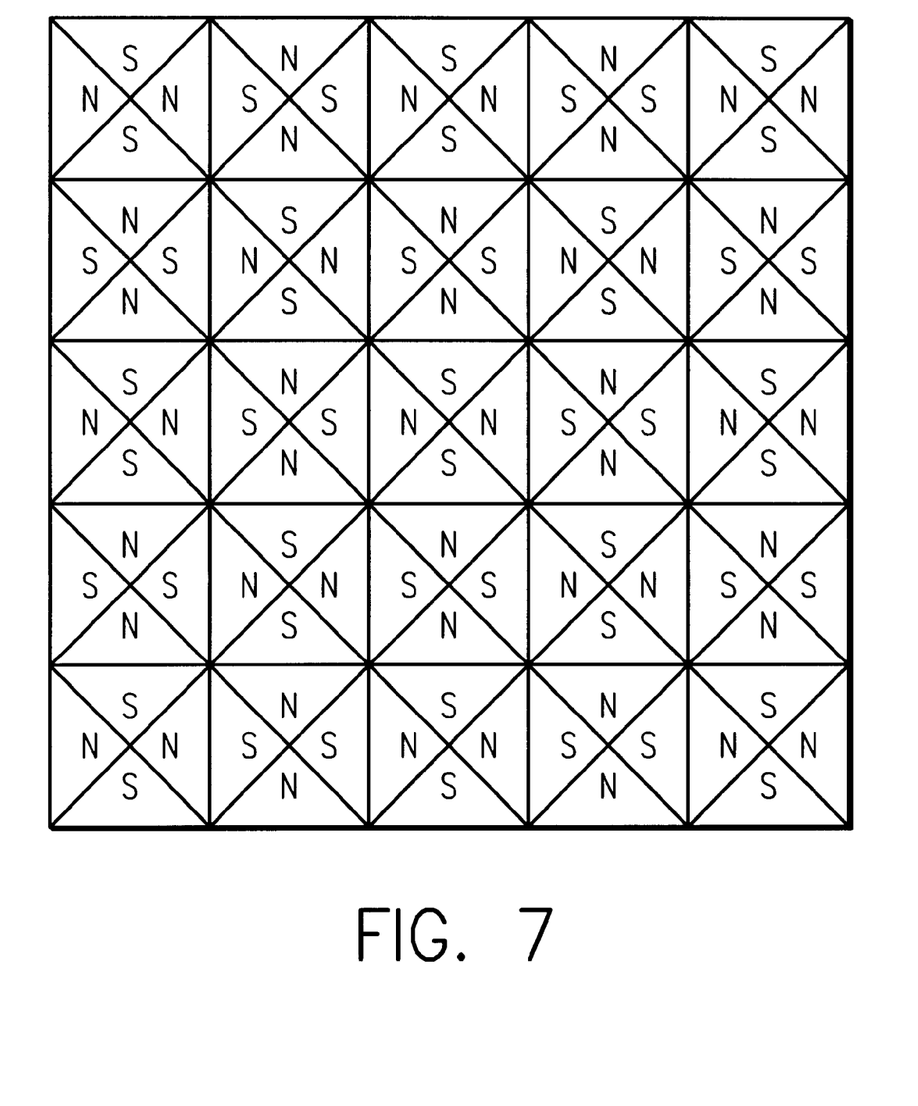
Figure 8:
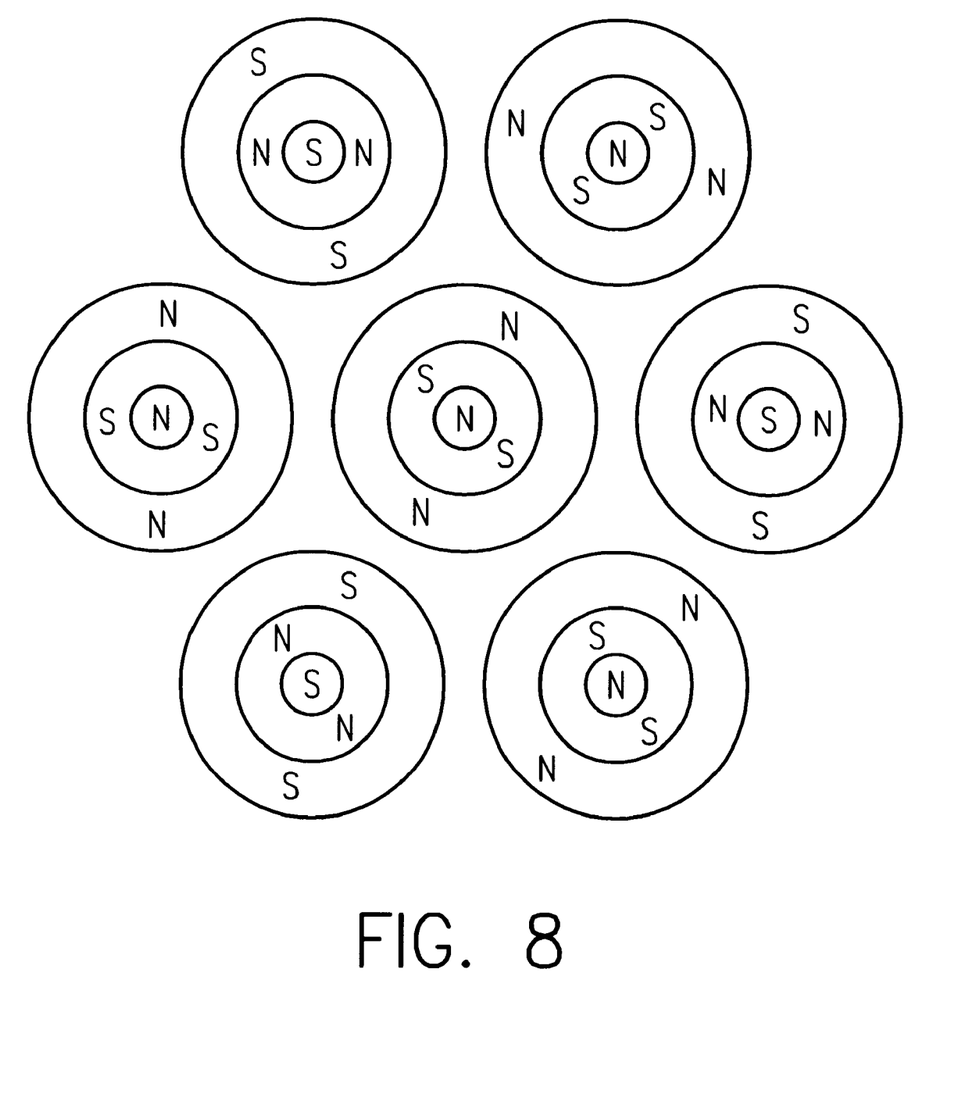
FIG. 8 shows a circular and toroidal alternating polarity magnetic field configuration that may be used in the flexible magnetic insole of FIG. 1.

As is set forth in the parent application for the present invention, namely Magnetic Wrap for Joints (indicated in the Cross-References to Related Applications section, above as U.S. patent application Ser. No. 09/038,508 filed Mar. 10, 1998), a two (2) roll rubber mill is used to mix together the magnetic ferrite with the elastic binder. This is shown in FIG. 3 as step 80.

Using a two-roll rubber mill as is known in the art, a slower roller is coated with elastic neoprene while the entire roller structure is maintained in a cool condition as by a ten-ton chiller. The rollers may be approximately twenty inches (20") in diameter and sixty inches (60") in length. Once neoprene has fully coated the slower roller, the magnetic ferrite (strontium ferrite) or other strongly magnetic material may be fed into the highly viscous neoprene.

The magnetic ferrite and other materials are mixed into the highly viscous neoprene during the rolling process as it is fed into the nip, or bank, formed between the upper and faster spinning roller and the lower and slower turning roller. In addition to the magnetic ferrite or other strongly magnetic material, stearic acid, a complex fatty acid such as that known currently in the trade as INT-21G (marketed as a member of the MoldWiz® line of internal lubricants and mold releases) as manufactured by Axel Plastics Research Laboratories, of Woodside, N.Y., and zinc oxide curatives may be mixed in. These substances may form the remainder of the materials used to form the flexible magnetic core.

In mixing the filler into the rolling neoprene, it is important to ensure that the INT-21G is not mixed in prematurely as it has a tendency to increase the viscosity of the rolling neoprene beyond that which is effective for working. Consequently, it is better to work in the magnetic ferrite first before adding too much of the INT-21G. One means by which this can be effected is by loading the feeder with the magnetic ferrite and then on top of the magnetic ferrite, adding the INT-21G, possibly with the stearic acid and zinc oxide curatives.

Once the mixture has been completely rolled and processed, portions of the rolled material, known as "pigs" in the art, are prepared from the roll. This is shown as step 82 in FIG. 3. When the neoprene is worked into a sufficiently mixed condition, the rollers are stopped. "Pigs" are pulled off in strips and rolled up into a chilled calendar for pre-forming prior to pressing. Each pig is calendared into a sheet of approximately 50/1000 of an inch by rolling it between two (2) rollers. During this pressing and rolling process, the material is heated at a temperature of over three hundred degrees Fahrenheit (300° F.) in order to provide for cross-linking and curing of the material.

Vulcanization occurs during the pressing process which may occur at approximately two hundred (200) tons pressure and 350° F. It should be noted that some forms of neoprene contain antioxidizing agents and the like to prevent oxidation of the magnetic ferrite. Additionally, the stearic acid helps to delay vulcanization so that it does not occur until intentionally induced during the pressing process. The zinc oxide curatives also help to cure the final product.

The resulting sheet is spooled upon a large spool or bobbin with sheets of nonadhesive paper or other light material separating the adjacent layers. As the pigs are calendared 84, a nylon mesh may be applied and embedded into the resulting thin sheet. 86. The nylon mesh provides structural support and reinforcement for the thin magnetizable sheet 86.

Sheets of the calendared material may now be unspooled for cutting and punching into usable sizes. After portions have been cut that are easily handled, the resulting sheet is magnetized by using a press incorporating ultra-strong permanent magnets 88. The sheet is placed between the two jaws of the magnetic press in an open brass envelope. The jaws are configured so that a north magnetic pole magnet on one side of the magnetic press faces a south magnetic pole magnet on its counterpart. The pressing process may occur at elevated pressures and temperatures. Magnetizing the sheet 86 at or near the Curie temperature aids in the magnetization process. Particularly, the flexible ferrite sheet may be elevated above the Curie temperature to enhance the magnetization process. Reducing the sheet temperature below the Curie point serves to fix magnetism in the sheet.

The open brass envelope is used so that the resulting magnetized flexible magnetic core sheet will not magnetically adhere to one side or the other of the magnetic press. The brass is generally non-ferromagnetic and serves as a means by which the magnetized sheet can be separated from the magnetic press. The magnetic press may additionally use high pressure in order to better impart its magnetic field and to further cure the flexible magnetic core material as by pressure. Once the magnetization process 88 has taken place, the resulting flexible magnetic core sheet is ready for lamination 90 with the leather upper 52 and the cushioning base 54 material.

As a further element of the method of manufacture of the magnetic insole 50 of the present invention, the perforation process 74 creates a number of stubs or cores that could interfere with the efficient processing. Generally, the punches used to create the perforations are able to eject the core material that has been punched out to create the perforations in the magnetic insole 50. These may be swept away by a whiskbroom or the like in order to keep clear the operating surface of the punch press.

As shown in FIGS. 4–8, a variety of regular and alternating magnetic field configurations may be achieved by using the magnetic press mentioned above with respect to the magnetization 88 of the flexible core material. The jaws of the magnetic press may reflect in mirror image the configurations shown in FIGS. 4–8.

Strontium ferrite is generally able to take on and maintain the magnetization imparted to it by the magnetic press. In so doing, it may form the alternating permanent magnets used in the magnetotherapeutic insole 50 of the present invention. Other strongly magnetic substances that are suitable for use in the present invention may also be used to good advantage, such as barium ferrite.

While the present invention has been described with regards to particular embodiments, it is recognized that additional variations of the present invention may be devised without departing from the inventive concept.

What is claimed is:

1. A flexible magnetic insole, comprising:
   a resilient upper, said resilient upper adapted to resiliently and durably engage a sole of a foot;
   a flexible magnetic core coupled to said resilient upper, said flexible magnetic core permanently magnetized with spatially-alternating magnetic polarities;
   said flexible magnetic core including permanent magnetic particle s embedded therein with said magnetic particles forming at least one magnetic zone of a first polarity and a plurality of magnetic zones of a second polarity;

said at least one magnetic zone of first polarity and said plurality of magnetic zones of second polarity being positioned contiguous with one another;

said at least one magnetic zone of first polarity being contiguous with three of said zones of second polarity, said at least one magnetic zone of first polarity being triangular in shape; and a cushioning base, said cushioning base coupled to said flexible magnetic core, said cushioning base providing cushioning for said foot; whereby said sole of said foot is subject to ongoing magneto-therapy by the flexible magnetic insole when the flexible magnetic insole is inserted in footwear worn on said foot.

2. The flexible magnetic insole of claim 1, comprising:

said resilient upper defining first ventilation holes;

said flexible magnetic core defining second ventilation holes;

said cushioning base defining third ventilation holes; and said first, second, and third ventilation holes being aligned; whereby the flexible magnetic insole allows ventilation of said insole via said ventilation holes.

3. The flexible magnetic insole of claim 1, wherein said resilient upper further comprises:

leather, said leather engaging said foot and providing a resilient surface withstanding wear exerted by said foot on the flexible magnetic insole.

4. The flexible magnetic insole of claim 1, wherein said flexible magnetic core further comprises:

ferromagnetic particles held in an elastic binder.

5. The flexible magnetic insole of claim 4, wherein said ferromagnetic particles are ferrite compounds selected from the group consisting of group II elements of the periodic table.

6. The flexible magnetic insole of claim 5, wherein said group II ferromagnetic particles are selected from the group consisting of strontium and barium.

7. The flexible magnetic insole of claim 4, wherein said group II ferromagnetic particles are strontium ferrite particles.

8. The flexible magnetic insole of claim 4, wherein said flexible magnetic core further comprises:

strontium ferrite, said strontium ferrite providing a highly magnetizable substrate for the flexible magnetic insole.

9. The flexible magnetic insole of claim 1, wherein said first polarity is selected from the group consisting of:

north polarity and south polarity.

10. A flexible magnetic insole, comprising:

a resilient upper, said resilient upper adapted to resiliently and durably engage a sole of a foot, said leather upper defining first ventilation holes;

a flexible magnetic core coupled to said leather upper, said flexible magnetic core permanently magnetized with spatially-alternating magnetic polarities, said flexible magnetic core defining second ventilation holes, said flexible magnetic core providing magnetic properties by ferromagnetic strontium ferrite particles held in an elastic binder;

said flexible magnetic core including permanent magnetic particles embedded therein with said magnetic particles forming at least one magnetic zone of a first polarity and a plurality of magnetic zones of a second polarity;

said at least one magnetic zone of first polarity and said plurality of magnetic zones of second polarity being positioned contiguous with one another;

said at least one magnetic zone of first polarity being contiguous with three of said zones of second polarity, said at least one magnetic zone of first polarity being triangular in shape; and a cushioning base, said cushioning base coupled to said flexible magnetic core, said cushioning base providing cushioning for said foot, said cushioning base defining third ventilation holes, said first, second, and third ventilation holes being aligned; whereby said sole of said foot is subject to ongoing magneto-therapy by the flexible magnetic insole when the flexible magnetic insole is inserted in footwear worn on said foot, the flexible magnetic insole allowing ventilation of said insole via said ventilation holes.

11. The flexible magnetic insole of claim 10, wherein said first polarity is selected from the group consisting of:

north polarity and south polarity.

* * * * *